US010688168B2

(12) United States Patent
Ballou, Jr. et al.

(10) Patent No.: US 10,688,168 B2
(45) Date of Patent: Jun. 23, 2020

(54) METHODS FOR INDUCING AN IMMUNE RESPONSE

(71) Applicant: GlaxoSmithKline Biologicals S.A., Rixensart (BE)

(72) Inventors: William Ripley Ballou, Jr., Rixensart (BE); Marie-Ange Demoitie, Rixensart (BE); Marie-Noelle Renelle Donner, Rixensart (BE); Nadia Ouaked, Rixensart (BE); Stephane Theophile Temmerman, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 0 days.

(21) Appl. No.: 15/300,852

(22) PCT Filed: Apr. 2, 2015

(86) PCT No.: PCT/EP2015/057423
§ 371 (c)(1),
(2) Date: Sep. 30, 2016

(87) PCT Pub. No.: WO2015/150567
PCT Pub. Date: Oct. 8, 2015

(65) Prior Publication Data
US 2017/0112914 A1    Apr. 27, 2017

(30) Foreign Application Priority Data

Apr. 2, 2014 (GB) .................................. 1405921.6

(51) Int. Cl.
A61K 39/015 (2006.01)
A61K 39/04 (2006.01)
A61K 39/29 (2006.01)
A61K 39/00 (2006.01)

(52) U.S. Cl.
CPC ............ *A61K 39/015* (2013.01); *A61K 39/04* (2013.01); *A61K 39/292* (2013.01); *A61K 2039/54* (2013.01); *A61K 2039/545* (2013.01); *A61K 2039/55555* (2013.01); *A61K 2039/55572* (2013.01); *A61K 2039/55577* (2013.01); *A61K 2039/575* (2013.01); *A61K 2039/70* (2013.01); *C12N 2730/10134* (2013.01); *Y02A 50/412* (2018.01)

(58) Field of Classification Search
None
See application file for complete search history.

(56) References Cited

U.S. PATENT DOCUMENTS

| 8,932,600 B2 * | 1/2015 | Blais ..................... | A61K 39/04 424/190.1 |
| --- | --- | --- | --- |
| 9,200,044 B2 * | 12/2015 | Blais ..................... | A61K 39/04 |
| 9,315,556 B2 * | 4/2016 | Brown ................... | A61K 39/04 |
| 9,352,030 B2 * | 5/2016 | Godart ................... | A61K 39/04 |
| 9,452,209 B2 * | 9/2016 | Ballou .................. | A61K 39/145 |
| 9,480,735 B2 * | 11/2016 | Mettens ................. | A61K 39/04 |
| 9,494,586 B2 * | 11/2016 | Feigner .................. | A61K 39/015 |
| 9,597,389 B2 * | 3/2017 | Ballou .................. | A61K 39/145 |
| 9,655,958 B2 * | 5/2017 | Coler ..................... | A61K 39/04 |
| 10,004,793 B2 * | 6/2018 | Aagaard ................ | A61K 39/04 |
| 10,039,823 B2 * | 8/2018 | Vandepapeliere ..... | A61K 39/00 |
| 10,105,430 B2 * | 10/2018 | Marchand ............. | C07K 14/35 |
| 10,286,053 B2 * | 5/2019 | Mettens ................. | C12N 9/88 |
| 10,441,648 B2 * | 10/2019 | Godart ................... | A61K 39/04 |
| 2011/0117119 A1 * | 5/2011 | Mettens ................. | A61K 39/04 424/190.1 |
| 2012/0294882 A1 * | 11/2012 | Blais ..................... | A61K 39/04 424/190.1 |
| 2013/0280289 A1 * | 10/2013 | Godart ................... | A61K 39/04 424/190.1 |
| 2014/0086948 A1 * | 3/2014 | Mettens ................. | A61K 39/04 424/190.1 |
| 2014/0178423 A1 * | 6/2014 | Mettens ................. | A61K 39/04 424/190.1 |
| 2014/0314802 A1 * | 10/2014 | Mettens ................. | A61K 39/04 424/190.1 |
| 2016/0220656 A1 * | 8/2016 | Godart ................... | A61K 39/04 |
| 2017/0043003 A1 * | 2/2017 | Aagaard ................ | A61K 39/04 |
| 2017/0065696 A9 * | 3/2017 | Coler ..................... | A61K 39/04 |
| 2017/0065697 A1 * | 3/2017 | Mettens ................. | A61K 39/04 |
| 2017/0112914 A1 * | 4/2017 | Ballou, Jr. ............. | A61K 39/04 |
| 2017/0136110 A1 * | 5/2017 | Ballou, Jr. ............. | A61K 39/015 |
| 2018/0216081 A1 * | 8/2018 | Colloca ................. | A61K 39/12 |
| 2018/0250375 A1 * | 9/2018 | Demoitie ............... | A61K 39/12 |
| 2018/0296505 A1 * | 10/2018 | Timmins .............. | A61K 9/0075 |
| 2019/0030154 A1 * | 1/2019 | Marchand ............. | A61K 39/04 |

FOREIGN PATENT DOCUMENTS

WO  WO 2010/010177 A1 *  1/2010
WO  WO 2010/010179 A1 *  1/2010
WO  WO 2010/010180 A1 *  1/2010

(Continued)

OTHER PUBLICATIONS

Homolka et al, PLoS One, 11(3):e0152200 published Mar. 24, 2016, 10 pages.*
Andersen, Trends in Microbiology, available online Dec. 1, 2006, 15/1:7-13.*
Brandt et al, Infection and Immunity, Nov. 2004, 72/11:6622-6632.*
Fujita et al, In: Therapeutic Delivery, Jun. 2012, 3/6:749-760.*
Gillard et al, Tuberculosis, 2016, 100:118-127.*
Hawkridge et al, Paediatric Respiratory Reviews, 2011, 12:46-51.*
Leroux-Roels et al, Clinical and Vaccine Immunology, Nov. 2010, 17/11:1763-1771.*
Reed et al, Microbes and Infection, Available online Apr. 14, 2005, 7:922-931.*

(Continued)

*Primary Examiner* — Nita M. Minnifield
(74) *Attorney, Agent, or Firm* — Joseph Schuller

(57) ABSTRACT

Methods and uses are provided for inducing an immune response comprising at least two administrations of an immunogenic composition comprising an M72 related antigen and wherein a subsequent administration is delayed.

12 Claims, 5 Drawing Sheets

Specification includes a Sequence Listing.

(56) References Cited

FOREIGN PATENT DOCUMENTS

| WO | 2012/080369 A1 | | 6/2012 |
|---|---|---|---|
| WO | WO 2012/080369 A1 | * | 6/2012 |
| WO | WO 2015/150567 A1 | * | 10/2015 |
| WO | WO 2017/017050 A1 | * | 2/2017 |

OTHER PUBLICATIONS

Skeiky et al, Journal of Immunology, 2004, 172:7618-7628.*
Heather Davis, In:New Generation Vaccines (ed M. Myron), 2010, pp. 263-271.*
Von Eschen et al, Human Vaccines, Jul. 2009, 5/7:475-482.*
Mortier et al. BMC Immunology (2015) 16:63, 14 pages.*
Montagnani et al. BMC Infectious Diseases 2014, 14(Suppl 1):S2, 9 pages.*
Ottenhoff THM, Kaufmann SHE (2012) Vaccines against Tuberculosis: Where Are We and Where Do We Need to Go? PLoS Pathog 8(5): e1002607. doi:10.1371/journal.ppat.1002607, published May 10, 2012, 12 pages.*
Ahmed et al, International Union of Biochemistry and Molecular Biology, vol. 67, No. 6, Jun. 2015, pp. 414-427, published online Jun. 24, 2015.*
Montoya et al, J. Clinical Immunology, 2013, 33:1360-1375.*
Mcshane, H. "Tuberculosis vaccines: beyond bacille Calmette-Guerin" Philosophical Transactions. Royal Society of London; Jan. 1, 2011; vol. 366 ; pp. 2782-2789.
Day, et al., "Induction and Regulation of T-Cell Immunity by the Novel Tuberculosis Vaccine M72/AS01 in South African Adults" American Journal of Respiratory and Critical Care Medicine; Aug. 15, 2013; vol. 188, No. 4; pp. 492-502.
Leroux-Roels, et al., "Improved CD4+ T cell responses to *Mycobacterium tuberculosis* in PPD-negative adults by M72/AS01 as compared to the M72/AS02 and Mtb72f/AS02 tuberculosis candidate vaccine formulations: A randomized trial" Vaccine; Apr. 1, 2013; vol. 31, No. 17; pp. 2196-2206.
Montoya, et al., "A Randomized, Controlled Dose-Finding Phase II Study of the M72/AS01 Candidate Tuberculosis Vaccine in Healthy PPD-Positive Adults" Journal of Clinical Immunology; Oct. 20, 2013; vol. 33, No. 8; pp. 1360-1375.

\* cited by examiner

Cytokine Profile of M72-specific CD4 T cells response- Pool of peptides M72 7dPII-7dPIII-77dPIII Cytokine profile of M72-specific CD8 T cells response- Pool of peptides M72 7dPII-7dPIII-77dPIII

SEQUENCE LISTING

```
<160> NUMBER OF SEQ ID NOS: 3

<210> SEQ ID NO 1
<211> LENGTH: 723
<212> TYPE: PRT
<213> ORGANISM: Artificial Sequence
<220> FEATURE:
<223> OTHER INFORMATION: M72 fusion protein

<400> SEQUENCE: 1

Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
    130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ser Pro Tyr
        195                 200                 205

Val Ala Trp Met Ser Val Thr Ala Gly Gln Ala Glu Leu Thr Ala Ala
    210                 215                 220

Gln Val Arg Val Ala Ala Ala Ala Tyr Glu Thr Ala Tyr Gly Leu Thr
225                 230                 235                 240
```

-continued

```
Val Pro Pro Val Ile Ala Glu Asn Arg Ala Glu Leu Met Ile Leu
        245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Met Phe
        275                 280                 285

Gly Tyr Ala Ala Ala Thr Ala Thr Ala Thr Leu Leu Pro Phe
290                 295                 300

Glu Glu Ala Pro Glu Met Thr Ser Ala Gly Leu Leu Glu Gln Ala
305                 310                 315                 320

Ala Ala Val Glu Glu Ala Ser Asp Thr Ala Ala Asn Gln Leu Met
                325                 330                 335

Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
        355                 360                 365

His Arg Ser Pro Ile Ser Asn Met Val Ser Met Ala Asn Asn His Met
    370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
            420                 425                 430

Ser Ser Gly Leu Gly Gly Val Ala Ala Asn Leu Gly Arg Ala Ala
        435                 440                 445

Ser Val Gly Ser Leu Ser Val Pro Gln Ala Trp Ala Ala Ala Asn Gln
    450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
                485                 490                 495

Gln Met Gly Ala Arg Ala Gly Gly Leu Ser Gly Val Leu Arg Val
            500                 505                 510

Pro Pro Arg Pro Tyr Val Met Pro His Ser Pro Ala Ala Gly Asp Ile
        515                 520                 525

Ala Pro Pro Ala Leu Ser Gln Asp Arg Phe Ala Asp Phe Pro Ala Leu
    530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
        595                 600                 605

Thr Tyr Gly Val Asp Val Val Gly Tyr Asp Arg Thr Gln Asp Val Ala
    610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Ala Met Gly Asn Ser Gly
                645                 650                 655

Gly Gln Gly Gly Thr Pro Arg Ala Val Pro Gly Arg Val Val Ala Leu
```

```
                    660                 665                 670
Gly Gln Thr Val Gln Ala Ser Asp Ser Leu Thr Gly Ala Glu Glu Thr
                675                 680                 685

Leu Asn Gly Leu Ile Gln Phe Asp Ala Ala Ile Gln Pro Gly Asp Ala
            690                 695                 700

Gly Gly Pro Val Val Asn Gly Leu Gly Gln Val Val Gly Met Asn Thr
705                 710                 715                 720

Ala Ala Ser

<210> SEQ ID NO 2
<211> LENGTH: 725
<212> TYPE: PRT
<213> ORGANISM: Artificial Sequence
<220> FEATURE:
<223> OTHER INFORMATION: M72 fusion protein (2-his)

<400> SEQUENCE: 2

Met His His Thr Ala Ala Ser Asp Asn Phe Gln Leu Ser Gln Gly Gly
1               5                   10                  15

Gln Gly Phe Ala Ile Pro Ile Gly Gln Ala Met Ala Ile Ala Gly Gln
            20                  25                  30

Ile Arg Ser Gly Gly Ser Pro Thr Val His Ile Gly Pro Thr Ala
        35                  40                  45

Phe Leu Gly Leu Gly Val Val Asp Asn Gly Asn Gly Ala Arg Val
    50                  55                  60

Gln Arg Val Val Gly Ser Ala Pro Ala Ala Ser Leu Gly Ile Ser Thr
65                  70                  75                  80

Gly Asp Val Ile Thr Ala Val Asp Gly Ala Pro Ile Asn Ser Ala Thr
                85                  90                  95

Ala Met Ala Asp Ala Leu Asn Gly His His Pro Gly Asp Val Ile Ser
            100                 105                 110

Val Thr Trp Gln Thr Lys Ser Gly Gly Thr Arg Thr Gly Asn Val Thr
        115                 120                 125

Leu Ala Glu Gly Pro Pro Ala Glu Phe Met Val Asp Phe Gly Ala Leu
    130                 135                 140

Pro Pro Glu Ile Asn Ser Ala Arg Met Tyr Ala Gly Pro Gly Ser Ala
145                 150                 155                 160

Ser Leu Val Ala Ala Ala Gln Met Trp Asp Ser Val Ala Ser Asp Leu
                165                 170                 175

Phe Ser Ala Ala Ser Ala Phe Gln Ser Val Val Trp Gly Leu Thr Val
            180                 185                 190

Gly Ser Trp Ile Gly Ser Ser Ala Gly Leu Met Val Ala Ala Ala Ser
        195                 200                 205

Pro Tyr Val Ala Trp Met Ser Val Thr Ala Gly Gln Ala Glu Leu Thr
    210                 215                 220

Ala Ala Gln Val Arg Val Ala Ala Ala Tyr Glu Thr Ala Tyr Gly
225                 230                 235                 240

Leu Thr Val Pro Pro Pro Val Ile Ala Glu Asn Arg Ala Glu Leu Met
                245                 250                 255

Ile Leu Ile Ala Thr Asn Leu Leu Gly Gln Asn Thr Pro Ala Ile Ala
            260                 265                 270

Val Asn Glu Ala Glu Tyr Gly Glu Met Trp Ala Gln Asp Ala Ala Ala
        275                 280                 285

Met Phe Gly Tyr Ala Ala Ala Thr Ala Thr Ala Thr Ala Thr Leu Leu
    290                 295                 300
```

```
Pro Phe Glu Glu Ala Pro Glu Met Thr Ser Ala Gly Gly Leu Leu Glu
305                 310                 315                 320

Gln Ala Ala Ala Val Glu Ala Ser Asp Thr Ala Ala Ala Asn Gln
            325                 330                 335

Leu Met Asn Asn Val Pro Gln Ala Leu Gln Gln Leu Ala Gln Pro Thr
                340                 345                 350

Gln Gly Thr Thr Pro Ser Ser Lys Leu Gly Gly Leu Trp Lys Thr Val
        355                 360                 365

Ser Pro His Arg Ser Pro Ile Ser Asn Met Val Ser Met Ala Asn Asn
370                 375                 380

His Met Ser Met Thr Asn Ser Gly Val Ser Met Thr Asn Thr Leu Ser
385                 390                 395                 400

Ser Met Leu Lys Gly Phe Ala Pro Ala Ala Ala Gln Ala Val Gln
            405                 410                 415

Thr Ala Ala Gln Asn Gly Val Arg Ala Met Ser Ser Leu Gly Ser Ser
                420                 425                 430

Leu Gly Ser Ser Gly Leu Gly Gly Val Ala Ala Asn Leu Gly Arg
        435                 440                 445

Ala Ala Ser Val Gly Ser Leu Ser Val Pro Gln Ala Trp Ala Ala Ala
450                 455                 460

Asn Gln Ala Val Thr Pro Ala Ala Arg Ala Leu Pro Leu Thr Ser Leu
465                 470                 475                 480

Thr Ser Ala Ala Glu Arg Gly Pro Gly Gln Met Leu Gly Gly Leu Pro
            485                 490                 495

Val Gly Gln Met Gly Ala Arg Ala Gly Gly Leu Ser Gly Val Leu
                500                 505                 510

Arg Val Pro Pro Arg Pro Tyr Val Met Pro His Ser Pro Ala Ala Gly
        515                 520                 525

Asp Ile Ala Pro Pro Ala Leu Ser Gln Asp Arg Phe Ala Asp Phe Pro
530                 535                 540

Ala Leu Pro Leu Asp Pro Ser Ala Met Val Ala Gln Val Gly Pro Gln
545                 550                 555                 560

Val Val Asn Ile Asn Thr Lys Leu Gly Tyr Asn Asn Ala Val Gly Ala
            565                 570                 575

Gly Thr Gly Ile Val Ile Asp Pro Asn Gly Val Val Leu Thr Asn Asn
                580                 585                 590

His Val Ile Ala Gly Ala Thr Asp Ile Asn Ala Phe Ser Val Gly Ser
        595                 600                 605

Gly Gln Thr Tyr Gly Val Asp Val Val Gly Tyr Asp Arg Thr Gln Asp
610                 615                 620

Val Ala Val Leu Gln Leu Arg Gly Ala Gly Gly Leu Pro Ser Ala Ala
625                 630                 635                 640

Ile Gly Gly Gly Val Ala Val Gly Glu Pro Val Val Ala Met Gly Asn
            645                 650                 655

Ser Gly Gly Gln Gly Gly Thr Pro Arg Ala Val Pro Gly Arg Val Val
                660                 665                 670

Ala Leu Gly Gln Thr Val Gln Ala Ser Asp Ser Leu Thr Gly Ala Glu
        675                 680                 685

Glu Thr Leu Asn Gly Leu Ile Gln Phe Asp Ala Ala Ile Gln Pro Gly
690                 695                 700

Asp Ala Gly Gly Pro Val Val Asn Gly Leu Gly Gln Val Val Gly Met
705                 710                 715                 720
```

Asn Thr Ala Ala Ser
            725

<210> SEQ ID NO 3
<211> LENGTH: 723
<212> TYPE: PRT
<213> ORGANISM: Artificial Sequence
<220> FEATURE:
<223> OTHER INFORMATION: Mtb72f

<400> SEQUENCE: 3

Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
    130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ser Pro Tyr
        195                 200                 205

Val Ala Trp Met Ser Val Thr Ala Gly Gln Ala Glu Leu Thr Ala Ala
    210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
        275                 280                 285

Gly Tyr Ala Ala Ala Thr Ala Thr Ala Thr Leu Leu Pro Phe
    290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Ala Asn Gln Leu Met
                325                 330                 335

Asn Asn Val Pro Gln Ala Leu Gln Gln Leu Ala Gln Pro Thr Gln Gly
            340                 345                 350

-continued

```
Thr Thr Pro Ser Ser Lys Leu Gly Gly Leu Trp Lys Thr Val Ser Pro
        355                 360                 365

His Arg Ser Pro Ile Ser Asn Met Val Ser Met Ala Asn Asn His Met
    370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
            420                 425                 430

Ser Ser Gly Leu Gly Gly Val Ala Ala Asn Leu Gly Arg Ala Ala
        435                 440                 445

Ser Val Gly Ser Leu Ser Val Pro Gln Ala Trp Ala Ala Ala Asn Gln
    450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
            485                 490                 495

Gln Met Gly Ala Arg Ala Gly Gly Leu Ser Gly Val Leu Arg Val
            500                 505                 510

Pro Pro Arg Pro Tyr Val Met Pro His Ser Pro Ala Ala Gly Asp Ile
        515                 520                 525

Ala Pro Pro Ala Leu Ser Gln Asp Arg Phe Ala Asp Phe Pro Ala Leu
        530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
            565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
        595                 600                 605

Thr Tyr Gly Val Asp Val Val Gly Tyr Asp Arg Thr Gln Asp Val Ala
    610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
        675                 680                 685

Leu Asn Gly Leu Ile Gln Phe Asp Ala Ala Ile Gln Pro Gly Asp Ser
    690                 695                 700

Gly Gly Pro Val Val Asn Gly Leu Gly Gln Val Val Gly Met Asn Thr
705                 710                 715                 720

Ala Ala Ser
```

METHODS FOR INDUCING AN IMMUNE RESPONSE

CROSS-REFERENCE TO RELATED APPLICATIONS

This application is filed pursuant to 35 U.S.C. § 371 as a United States National Phase Application of International Application No. PCT/EP2015/057423 filed 2 Apr. 2015, which claims priority to GB 1405921.6 filed 2 Apr. 2014.

TECHNICAL FIELD

The present invention relates to methods for inducing an immune response, in particular methods for immunisation comprising at least two administrations of an adjuvanted immunogenic composition wherein a subsequent administration is delayed.

BACKGROUND OF THE INVENTION

Vaccination is one of the most effective methods for preventing infectious diseases. However, a single administration of an antigen is often not sufficient to confer optimal immunity and/or a long-lasting response. Approaches for establishing strong and lasting immunity to specific pathogens include addition of adjuvants to vaccines and/or repeated vaccination, i.e. boosting an immune response by administration of one or more further doses of antigen. Such further administrations may be performed with the same vaccine (homologous boosting) or with a different vaccine (heterologous boosting). The most common approach for homologous boosting is not only to administer the same vaccine, but also to administer it in the same dose as the earlier administration.

Tuberculosis (TB) is a chronic infectious disease caused by infection with *Mycobacterium tuberculosis* and other *Mycobacterium* species. It is a major disease in developing countries, as well as an increasing problem in developed areas of the world.

The protein antigens Mtb72f and M72 (described, for example, in international patent applications WO2006/117240 and WO2012/080369 which are incorporated herein by reference) or fragments or derivatives thereof are protein antigens of potential benefit for the treatment or prevention of tuberculosis. Previous investigations have led to M72 being administered in humans in conjunction with the immunostimulants 3-O-deacylated monophosphoryl lipid A (3D-MPL) and QS21 in a liposomal formulation and in a 0,1 month schedule using 10 ug M72, 25 ug 3D-MPL and 25 ug QS21 (Leroux-Roels et al Vaccine 2013 31 2196-2206, Montoya et al *J. Clin. Immunol.* 2013 33(8): 1360-1375).

A candidate vaccine utilising the antigen M72 is currently in a Phase IIB trial (ClinicalTrials.gov Identifier: NCT01755598) to evaluate the protective efficacy of two doses against pulmonary TB, as compared to placebo, in adults aged 18-50 living in TB endemic countries.

There remains a need for novel methods of immunising against diseases, including tuberculosis, which are highly efficacious, safe, cost-effective, long-lasting and induce a broad spectrum of cross-reactive immune responses.

SUMMARY OF THE INVENTION

It has now surprisingly been found that, in a multi-dose method of immunisation using an adjuvanted M72 vaccine, the immunisation was more effective when a subsequent dose (booster dose) was delayed as compared to an earlier dose (primer dose). The adjuvant used comprised a TLR4 agonist, 3D-MPL, and an immunologically active saponin fraction, QS21.

Accordingly, in a first aspect of the invention, there is provided a method for inducing an immune response in a subject comprising administration of a first immunogenic composition comprising an M72 related antigen and a first adjuvant to the subject, followed by administration of a second immunogenic composition comprising an M72 related antigen to the subject, wherein the first adjuvant comprises a TLR agonist and/or an immunologically active saponin and wherein the interval between the first and second administrations is between two months and five years.

Optionally, the second immunogenic composition comprises a second adjuvant wherein the second adjuvant comprises a TLR agonist and/or an immunologically active saponin. Suitably, the second adjuvant comprises a TLR agonist and/or an immunologically active saponin and has at least one of these two components in common with the first adjuvant.

BRIEF DESCRIPTION OF THE SEQUENCE IDENTIFIERS

Figure 1:
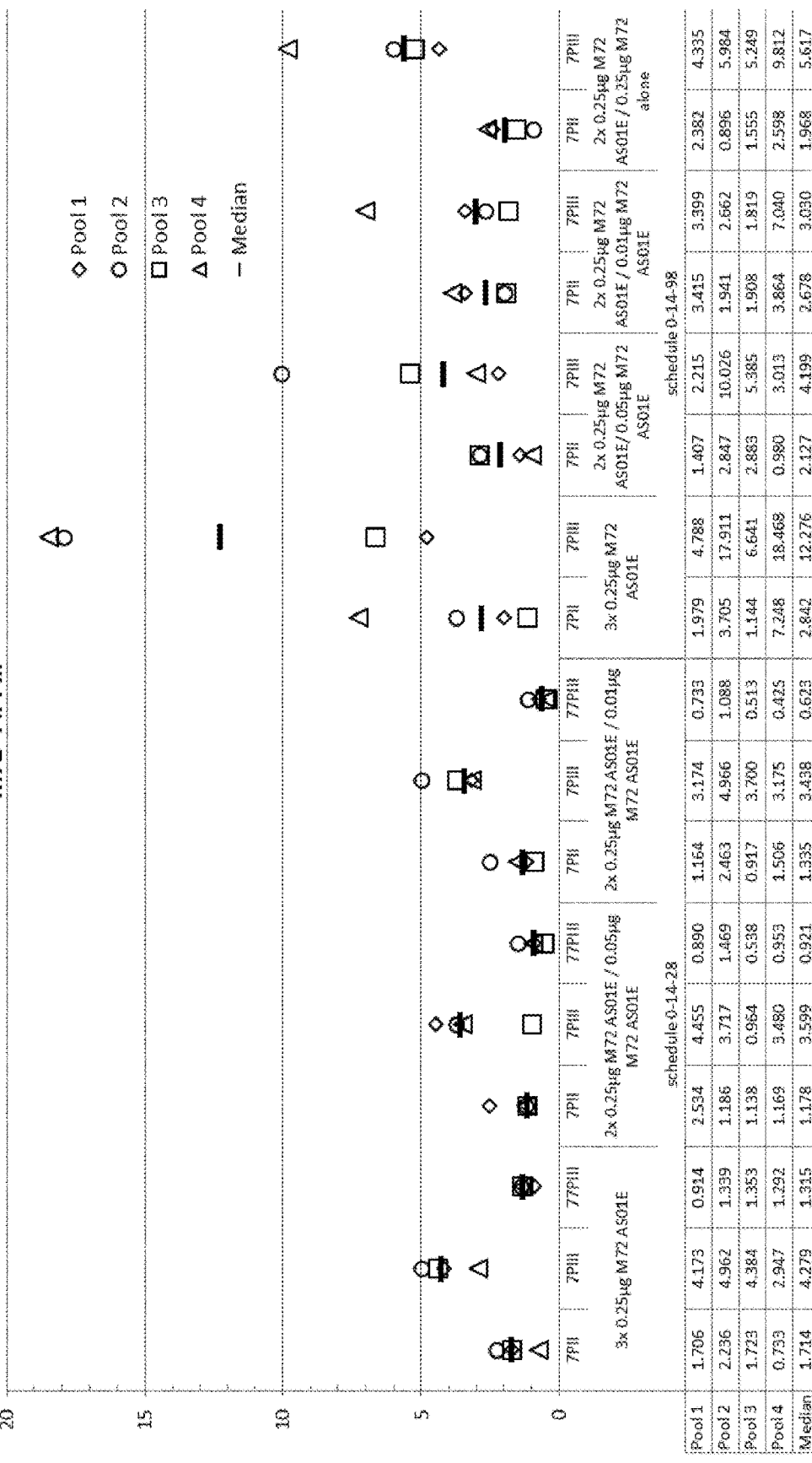
FIG. 1: CD4 T cell responses from mice administered M72 in standard and delayed regimes

SEQ ID No. 1: polypeptide sequence of M72

SEQ ID No. 2: polypeptide sequence of M72 protein with two N-terminal His residues SEQ ID No. 3: polypeptide sequence of Mtb72f

DETAILED DESCRIPTION

Tuberculosis (TB) is a chronic infectious disease caused by infection with *Mycobacterium tuberculosis* and other *Mycobacterium* species. It is a major disease in developing countries, as well as an increasing problem in developed areas of the world. More than 2 billion people are believed to be infected with TB bacilli, with about 9 million new cases of TB and 1.5 million deaths each year (World Health Organisation *Tuberculosis Facts* 2014). 10% of those infected with TB bacilli will develop active TB, each person with active TB infecting an average of 10 to 15 others per year.

*Mycobacterium tuberculosis* infects individuals through the respiratory route. Alveolar macrophages engulf the bacterium, but it is able to survive and proliferate by inhibiting phagosome fusion with acidic lysosomes. A complex immune response involving CD4+ and CD8+ T cells ensues, ultimately resulting in the formation of a granuloma. Central to the success of *Mycobacterium tuberculosis* as a pathogen is the fact that the isolated, but not eradicated, bacterium may persist for long periods, leaving an individual vulnerable to the later development of active TB.

Fewer than 5% of infected individuals develop active TB in the first years after infection. The granuloma can persist for decades and is believed to contain live *Mycobacterium tuberculosis* in a state of dormancy, deprived of oxygen and nutrients. However, recently it has been suggested that the majority of the bacteria in the dormancy state are located in non-macrophage cell types spread throughout the body (Locht et al, *Expert Opin. Biol. Ther.* 2007 7(11):1665-1677). The development of active TB occurs when the balance between the host's natural immunity and the pathogen changes, for example as a result of an immunosuppressive event (Anderson P *Trends in Microbiology* 2007 15(1): 7-13; Ehlers S *Infection* 2009 37(2):87-95).

A dynamic hypothesis describing the balance between latent TB and active TB has also been proposed (Cardana P-J *Inflammation & Allergy-Drug Targets* 2006 6:27-39; Cardana P-J *Infection* 2009 37(2):80-86).

Although an infection may be asymptomatic for a considerable period of time, the active disease is most commonly manifested as an acute inflammation of the lungs, resulting in tiredness, weight loss, fever and a persistent cough. If untreated, serious complications and death typically result.

Tuberculosis can generally be controlled using extended antibiotic therapy, although such treatment is not sufficient to prevent the spread of the disease. Actively infected individuals may be largely asymptomatic, but contagious, for some time. In addition, although compliance with the treatment regimen is critical, patient behaviour is difficult to monitor. Some patients do not complete the course of treatment, which can lead to ineffective treatment and the development of drug resistance.

Multidrug-resistant TB (MDR-TB) is a form which fails to respond to first line medications. 3.3% of all TB cases are MDR-TB, with an estimated 440,000 new MDR-TB cases occurring each year. Extensively drug-resistant TB (XDR-TB) occurs when resistance to second line medications develops on top of resistance to first line medications. The virtually untreatable XDR-TB has been confirmed in 58 countries (World Health Organisation *Tuberculosis Facts* 2010).

Even if a full course of antibiotic treatment is completed, infection with *M. tuberculosis* may not be eradicated from the infected individual and may remain as a latent infection that can be reactivated. In order to control the spread of tuberculosis, an effective vaccination programme and accurate early diagnosis of the disease are of utmost importance.

Currently, vaccination with attenuated live bacteria is the most widely used method for inducing protective immunity. The most common *Mycobacterium* employed for this purpose is *Bacillus Calmette-Guerin* (BCG), an avirulent strain of *M. bovis* which was first developed over 60 years ago. It is administrated at birth in TB endemic regions. However, the safety and efficacy of BCG is a source of controversy—while protecting against severe disease manifestation in children, the efficacy of BCG against disease is variable. Additionally, some countries, such as the United States, do not vaccinate the general public with this agent.

Several of the proteins which are strongly expressed during the early stages of *Mycobacterium* infection have been shown to provide protective efficacy in animal vaccination models. However, vaccination with antigens which are highly expressed during the early stages of infection may not provide an optimal immune response for dealing with later stages of infection. Adequate control during latent infection may require T cells which are specific for the particular antigens which are expressed at that time. Post-exposure vaccines which directly target the dormant persistent bacteria may aid in protecting against TB reactivation, thereby enhancing TB control, or even enabling clearance of the infection. A vaccine targeting latent TB could therefore significantly and economically reduce global TB infection rates.

Subunit vaccines based on late stage antigens could also be utilised in combination with early stage antigens to provide a multiphase vaccine. Alternatively, early and/or late stage antigens could be used to complement and improve BCG vaccination (either by boosting the BCG response or through the development of advanced recombinant BCG strains).

Mtb72f and M72 are protein antigens of potential benefit for the treatment or prevention of tuberculosis. Mtb72f has been shown to provide protection in a number of animal models (see, for example: Brandt et al *Infect. Immun.* 2004 72(11):6622-6632; Skeiky et al *J. Immunol.* 2004 172:7618-7628; Tsenova et al *Infect. Immun.* 2006 74(4):2392-2401). Mtb72f has also been the subject of clinical investigations (Von Eschen et al 2009 *Human Vaccines* 5(7):475-482). M72 is an improved antigen which incorporates a single serine to alanine mutation relative to Mtb72f, resulting in improved stability characteristics. M72 related antigens have also been shown to be of value in a latent TB model (international patent application WO2006/117240, incorporated herein by reference). Previous clinical investigations have led to M72 being administered in humans in conjunction with the immunostimulants 3-O-deacylated monophosphoryl lipid A (3D-MPL) and QS21 in a liposomal formulation and in a 0,1 month schedule using 10 ug M72, 25 ug 3D-MPL and 25 ug QS21 (see, for example, Leroux-Roels et al Vaccine 2013 31 2196-2206, Montoya et al *J. Clin. Immunol.* 2013 33(8): 1360-1375).

A candidate vaccine utilising the antigen M72 is currently in a Phase IIB trial (ClinicalTrials.gov Identifier: NCT01755598) to evaluate the protective efficacy of two doses against pulmonary TB, as compared to placebo, in adults aged 18-50 living in TB endemic countries. Nevertheless, a need for improved vaccination approaches remains.

In a first aspect, there is provided a method for inducing an immune response in a subject comprising administration of a first immunogenic composition comprising an M72 related antigen and a first adjuvant to the subject, followed by administration of a second immunogenic composition comprising an M72 related antigen to the subject, wherein the first adjuvant comprises a TLR agonist and/or an immunologically active saponin and wherein the interval between the first and second administrations is between two months and five years.

As used herein, administration of a first composition "followed by" administration of a second composition indicates that a time interval has elapsed between administration of the first composition and administration of the second composition.

Also provided is a first immunogenic composition comprising an M72 related antigen and a first adjuvant, wherein the first adjuvant comprises a TLR agonist and/or an immunologically active saponin, for use in a method for inducing an immune response in a subject, said method comprising administration of the first immunogenic composition to the subject, followed by administration of a second immunogenic composition comprising an M72 related antigen to the subject, and wherein the interval between the first and second administrations is between two months and five years.

Similarly, there is provided a second immunogenic composition comprising an M72 related antigen, for use in a method for inducing an immune response in a subject, said method comprising administration of a first immunogenic composition comprising an M72 related antigen and a first adjuvant, wherein the first adjuvant comprises a TLR agonist and/or an immunologically active saponin, to a subject, followed by administration of the second immunogenic composition to the subject, and wherein the interval between the first and second administrations is between two months and five years.

Further, there is provided the use of a first immunogenic composition comprising an M72 related antigen and a first adjuvant, wherein the first adjuvant comprises a TLR agonist and/or an immunologically active saponin, in the manufacture of a medicament for use in a method of inducing an immune response in a subject, said method comprising administration of the first immunogenic composition to the subject, followed by administration of a second immunogenic composition comprising an M72 related antigen to the subject, and wherein the interval between the first and second administrations is between two months and five years.

Additionally, there is provided the use of a second immunogenic composition, in the manufacture of a medicament for use in a method of inducing an immune response in a subject, said method comprising administration of a first immunogenic composition comprising an M72 related antigen and a first adjuvant, wherein the first adjuvant comprises a TLR agonist and/or an immunologically active saponin to the subject, followed by administration of the second immunogenic composition comprising an M72 related antigen to the subject, and wherein the interval between the first and second administrations is between two months and five years.

Optionally, the second immunogenic composition comprises a second adjuvant wherein the second adjuvant comprises a TLR agonist and/or an immunologically active saponin. Suitably, the second adjuvant comprises a TLR agonist and/or an immunologically active saponin and has at least one of these two components in common with the first adjuvant.

Suitably, the subject is a human.

Typically, the aim of the method of the invention is to induce a protective immune response, i.e. immunise or vaccinate the subject against a related pathogen. The invention may therefore be applied for the prophylaxis, treatment or amelioration of infection by mycobacteria, such as infection by *Mycobacterium tuberculosis*. In particular the invention may be provided for the purpose of:

prophylaxis of active tuberculosis due to infection or reactivation, such as by administering to a subject who is uninfected, or alternatively a subject who has a latent infection;

prophylaxis of latent tuberculosis, such as by administering to a subject who is uninfected;

treating latent tuberculosis;

preventing or delaying reactivation of tuberculosis, especially the delay of TB reactivation, for example by a period of months, years or indefinitely; or treating active tuberculosis.

The term "active infection" refers to an infection, e.g. infection by *M. tuberculosis*, with manifested disease symptoms and/or lesions, suitably with manifested disease symptoms.

The terms "inactive infection", "dormant infection" or "latent infection" or "latent tuberculosis" refer to an infection, e.g. infection by *M. tuberculosis*, without manifested disease symptoms and/or lesions, suitably without manifested disease symptoms. A subject with latent infection will suitably be one which tests positive for infection, e.g. by PPD or T cell based assays, but which has not demonstrated the disease symptoms and/or lesions which are associated with an active infection.

The term "primary tuberculosis" refers to clinical illness, e.g., manifestation of disease symptoms, directly following infection, e.g. infection by *M. tuberculosis*. See, *Harrison's Principles of Internal Medicine*, Chapter 150, pp. 953-966 (16th ed., Braunwald, et al., eds., 2005).

The terms "secondary tuberculosis" or "postprimary tuberculosis" refer to the reactivation of a dormant, inactive or latent infection, e.g. infection by *M. tuberculosis*. See, *Harrison's Principles of Internal Medicine*, Chapter 150, pp. 953-966 (16th ed., Braunwald, et al., eds., 2005).

The term "tuberculosis reactivation" refers to the later manifestation of disease symptoms in an individual that tests positive for infection (e.g. in a tuberculin skin test, suitably in an in vitro T cell based assay) test but does not have apparent disease symptoms. Suitably the individual will not have been re-exposed to infection. The positive diagnostic test indicates that the individual is infected, however, the individual may or may not have previously manifested active disease symptoms that had been treated sufficiently to bring the tuberculosis into an inactive or latent state.

Suitability the immunogenic compositions are administered to a subject who is uninfected or who has a latent infection by mycobacteria, such as infection by *Mycobacterium tuberculosis*.

In some embodiments, the subject has previously been vaccinated with BCG.

In some embodiments, the subject has previously been infected with *M. tuberculosis*.

Antigens of Use in the Invention.

As used herein the term 'M72 related antigen' refers to the M72 protein provided in SEQ ID No: 1 or an immunogenic derivative thereof. As used herein the term "derivative" refers to an antigen that is modified relative to the reference sequence. Immunogenic derivatives are sufficiently similar to the reference sequence to retain the immunogenic properties of the reference sequence and remain capable of allowing an immune response to be raised against the reference sequence. A derivative may, for example, comprise a modified version of the reference sequence or alternatively may consist of a modified version of the reference sequence.

The M72 related antigen may for example contain fewer than 1500 amino acid residues, such as fewer than 1200 amino acid residues, in particular less than 1000 amino acid residues, especially fewer than 800 amino acid residues.

T cell epitopes are short contiguous stretches of amino acids which are recognised by T cells (e.g. CD4+ or CD8+ T cells). Identification of T cell epitopes may be achieved through epitope mapping experiments which are known to the person skilled in the art (see, for example, Paul, *Fundamental Immunology*, 3rd ed., 243-247 (1993); Beiβbarth et al *Bioinformatics* 2005 21(Suppl. 1):i29-i37). In a diverse out-bred population, such as humans, different HLA types mean that particular epitopes may not be recognised by all members of the population. As a result of the crucial involvement of the T cell response in tuberculosis, to maximise the level of recognition and scale of immune response, an immunogenic derivative of M72 is desirably one which contains the majority (or suitably all) T cell epitopes intact.

The skilled person will recognise that individual substitutions, deletions or additions to the M72 protein which alters, adds or deletes a single amino acid or a small percentage of amino acids is an "immunogenic derivative" where the alteration(s) results in the substitution of an amino acid with a functionally similar amino acid or the substitution/deletion/addition of residues which do not substantially impact the immunogenic function.

Conservative substitution tables providing functionally similar amino acids are well known in the art. In general, such conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* 1984).

Suitably such substitutions do not occur in the region of an epitope, and do not therefore have a significant impact on the immunogenic properties of the antigen.

Immunogenic derivatives may also include those wherein additional amino acids are inserted compared to the reference sequence. Suitably such insertions do not occur in the region of an epitope, and do not therefore have a significant impact on the immunogenic properties of the antigen. One example of insertions includes a short stretch of histidine residues (e.g. 2-6 residues) to aid expression and/or purification of the antigen in question.

Immunogenic derivatives include those wherein amino acids have been deleted compared to the reference sequence. Suitably such deletions do not occur in the region of an epitope, and do not therefore have a significant impact on the immunogenic properties of the antigen.

The skilled person will recognise that a particular immunogenic derivative may comprise substitutions, deletions and additions (or any combination thereof).

The terms "identical" or percentage "identity," in the context of two or more polypeptide sequences, refer to two or more sequences or sub-sequences that are the same or have a specified percentage of amino acid residues that are the same (i.e., 70% identity, optionally 75%, 80%, 85%, 90%, 95%, 98% or 99% identity over a specified region), when compared and aligned for maximum correspondence over a comparison window, or designated region as measured using one of the following sequence comparison algorithms or by manual alignment and visual inspection. This definition also refers to the compliment of a test sequence. Optionally, the identity exists over a region that is at least 500 amino acids in length, such as at least 600 amino acids or at least 700 amino acids. Suitably, the comparison is performed over a window corresponding to the entire length of the reference sequence (as opposed to the derivative sequence).

For sequence comparison, one sequence acts as the reference sequence, to which the test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percentage sequence identities for the test sequences relative to the reference sequence, based on the program parameters.

A "comparison window", as used herein, refers to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerised implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984)).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

In any event, immunogenic derivatives of a polypeptide sequence will have essentially the same activity as the reference sequence. By essentially the same activity is meant at least 50%, suitably at least 75% and especially at least 90% activity of the reference sequence in an in vitro restimulation assay of PBMC or whole blood with specific antigens (e.g. restimulation for a period of between several hours to up to two weeks, such as up to one day, 1 day to 1 week or 1 to 2 weeks) that measures the activation of the cells via lymphoproliferation, production of cytokines in the supernatant of culture (measured by ELISA, CBA etc) or characterisation of T and B cell responses by intra and extracellular staining (e.g. using antibodies specific to immune markers, such as CD3, CD4, CD8, IL2, TNF-alpha, IFN-gamma, CD40L, CD69 etc) followed by analysis with a flowcytometer. Suitably, by essentially the same activity is meant at least 50%, suitably at least 75% and especially at least 90% activity of the reference sequence in a T cell proliferation and/or IFN-gamma production assay.

Particular derivatives of the M72 protein include those with additional His residues at the N-terminus (e.g. two His residues, as provided in SEQ ID No: 2; or a polyhistidine tag of five or particularly six His residues, which may be used for nickel affinity purification). Mtb72f (SEQ ID No: 3) which contains the original serine residue that has been mutated in M72, is a further derivative of M72, as are Mtb72f proteins with additional His residues at the N-terminus (e.g. two His residues; or a polyhistidine tag of five or particularly six His residues, which may be used for nickel affinity purification).

Suitably an M72 related antigen will comprise, such as consist of, a sequence having at least 70% identity to SEQ ID No. 1, such as at least 80%, in particular at least 90%, especially at least 95%, such as at least 98%, for example at least 99%.

Typical M72 related antigens will comprise, such as consist of, an immunogenic derivative of SEQ ID No: 1 or 2 having a small number of deletions, insertions and/or substitutions. Examples are those having deletions of up to 5 residues at 0-5 locations, insertions of up to 5 residues at 0-5 five locations and substitutions of up to 20 residues.

Other immunogenic derivatives of M72 are those comprising, such as consisting of, a fragment of SEQ ID No: 1 or 2 which is at least 300 amino acids in length, such as at least 350 amino acids in length, such as at least 400 amino acids in length, such as at least 500 amino acids in length, such as at least 600 amino acids in length or at least 700 amino acids in length. As M72 is a fusion protein derived from two individual antigens, any fragment of at least 300 residues will comprise a plurality of epitopes from the full length sequence (Skeiky et al *J. Immunol.* 2004 172:7618-7628; Skeiky Infect. Immun. 1999 67(8):3998-4007; Dillon *Infect. Immun.* 1999 67(6):2941-2950). In some embodiments the immunogenic derivative of M72 comprises at least 300 residues from Mtb39A.

In particular embodiments the M72 related antigen will comprise residues 2-723 of SEQ ID No. 1, for example comprise (or consist of) SEQ ID No. 1 or 2.

M72 related antigens may be prepared by methods previously described (WO2006/117240) or methods analogous thereto.

The immunogenic compositions may comprise one or more further antigenic components. Additional antigenic components may be intended to strengthen or complement the immune responses solicited by the M72 related antigen in the field of tuberculosis prevention and therapy or additional antigens could be associated with other pathogens and are intended for administration with the M72 related antigen for reasons of convenience. Where a number of antigenic components are present within the formulation, these may be provided in the form of individual polypeptides or fusion proteins. In some circumstances additional antigenic components may be provided as a polynucleotide (or polynucleotides).

The antigen is a *M. tuberculosis* antigen, such as the M72 antigen, e.g. the antigen described in WO2006/117240, which granted as U.S. Pat. No. 8,470,338 and which is incorporated by reference for the purpose of describing suitable proteins for use in the present invention.

Typically for administration to humans the first and second immunogenic compositions will comprise between 1 ug and 100 ug of M72 related antigen, such as between 1 ug and 50 ug. Suitably the first immunogenic composition will contain between 1 ug and 50 ug of M72 related antigen (such as between 5 ug and 50 ug), especially between 1 ug and 20 ug (such as between 5 ug and 20 ug) and in particular around or exactly 10 ug.

In some embodiments the second immunogenic composition will contain the same amount of M72 related antigen as the first immunogenic composition. For example, the second immunogenic composition will contain between 1 ug and 50 ug of M72 related antigen (such as between 5 ug and 50 ug), especially between 1 ug and 20 ug (such as between 5 ug and 20 ug) and in particular around or exactly 10 ug.

In other embodiments the second immunogenic composition will contain a reduced amount of M72 related antigen relative to the first immunogenic composition. For example, the second immunogenic composition will contain between 1 ug and 40 ug of M72 related antigen (such as between 2 ug and 40 ug), especially between 1 ug and 16 ug (such as between 2 ug and 16 ug) and in particular less than 10 ug (such as 1 to 8 ug).

In one embodiment, the lower amount of the M72 related antigen in the second immunogenic composition is an at least 10% lower, such as an at least 25% lower, e.g. an at least two fold lower, such as an at least three fold lower, e.g. an at least four fold lower, such as an at least five fold lower, e.g. an at least six fold lower, such as an at least seven fold lower, e.g. an at least eight fold lower, such as an at least nine fold lower, e.g. an at least ten fold lower, amount than in the first immunogenic composition.

The amount of the M72 related antigen in the second immunogenic composition is typically between 5/4 (i.e. 125%) and 1/10 (i.e. 10%) of that in the first immunogenic composition.

In one embodiment of the invention, the first and second immunogenic compositions contain the same M72 related antigen.

In some embodiments all antigens in the first and second immunogenic compositions are the same.

Adjuvants for Use in the Method of the Invention

As described above, in one aspect of the invention, the first adjuvant comprises a TLR agonist and/or an immunologically active saponin.

Thus, in one embodiment, the first adjuvant comprises a TLR agonist. In another embodiment, the first adjuvant comprises an immunologically active saponin. In yet another embodiment, the first adjuvant comprises a TLR agonist and an immunologically active saponin.

In another aspect, the first adjuvant and second adjuvant comprise a TLR agonist and/or an immunologically active saponin and have at least one of these two components in common.

Thus, in one embodiment, the first adjuvant and second adjuvant both comprise a TLR agonist. In another embodiment, the first adjuvant and second adjuvant both comprise an immunologically active saponin. In yet another embodiment, the first adjuvant and second adjuvant both comprise a TLR agonist and an immunologically active saponin.

In one embodiment, the first adjuvant and the second adjuvant consist of the same components. Thus, in such an embodiment, the components of both adjuvants are the same, although not necessarily in the same relative proportions. For example, the first adjuvant and the second adjuvant may both consists of a TLR agonist and a saponin in a liposomal formulation, but the ratio of TLR agonist to saponin may be 5:1 in the first adjuvant and 1:1 in the second adjuvant, 4:1 in the first adjuvant and 1:1 in the second adjuvant, 3:1 in the first adjuvant and 2:1 in the second adjuvant, 1:1 in the first adjuvant and 1:1 in the second adjuvant.

In another embodiment, the first adjuvant and second adjuvant consist of the same components and the relative proportions of these components are the same. However, in such an embodiment, while the relative proportions of the adjuvant components are the same, the absolute amounts of these components may differ between the first and second immunogenic compositions. For example the absolute amounts of all components in the second adjuvant may e.g. be one fifth of the absolute amounts of all components in the first adjuvant.

As described above, in one embodiment, the second adjuvant contains a lower amount of the common component (i.e. a lower amount of the TLR agonist or a lower amount of the saponin or a lower amount of both) than the first adjuvant.

In one embodiment, the lower amount of the common component in the second adjuvant is an at least 10% lower, such as an at least 25% lower, e.g. an at least two fold lower, such as an at least three fold lower, e.g. an at least four fold lower, such as an at least five fold lower, e.g. an at least six fold lower, such as an at least seven fold lower, e.g. an at least eight fold lower, such as an at least nine fold lower, e.g. an at least ten fold lower, such as an at least 15 fold lower, e.g. an at least 20 fold lower amount than in the first adjuvant.

In another embodiment, the lower amount of the common component in the second adjuvant is a between 2 and 50 fold lower, such as a between 2 and 20 fold lower, e.g. a between 2 and 15 fold lower, such as a between 2 and 10 fold lower, e.g. a between 3 and 7 fold lower, such as a between 4 and 6 fold lower amount than in the first adjuvant.

The amount of the common adjuvant component (such as all common adjuvant components) in the second immunogenic composition is typically between 5/4 (i.e. 125%) and 1/10 (i.e. 10%) of that in the first immunogenic composition.

As described above, in one embodiment, the first adjuvant and second adjuvant comprise a TLR (Toll-like receptor) agonist. The use of TLR agonists in adjuvants is well-known in art and has been reviewed e.g. by Lahiri et al. (2008) Vaccine 26:6777. TLRs that can be stimulated to achieve an adjuvant effect include TLR2, TLR4, TLR5, TLR7, TLR8 and TLR9. TLR2, TLR4, TLR7 and TLR8 agonists, particularly TLR4 agonists, are preferred.

Suitable TLR4 agonists include lipopolysaccharides, such as monophosphoryl lipid A (MPL) and 3-O-deacylated monophosphoryl lipid A (3D-MPL). U.S. Pat. No. 4,436,727 discloses MPL and its manufacture. U.S. Pat. No. 4,912,094 and reexamination certificate B1 4,912,094 discloses 3D-MPL and a method for its manufacture. Another TLR4 agonist is glucopyranosyl lipid adjuvant (GLA), a synthetic lipid A-like molecule (see, e.g. Fox et al. (2012) Clin. Vaccine Immunol 19:1633). In a further embodiment, the TLR4 agonist may be a synthetic TLR4 agonist such as a synthetic disaccharide molecule, similar in structure to MPL and 3D-MPL or may be synthetic monosaccharide molecules, such as the aminoalkyl glucosaminide phosphate (AGP) compounds disclosed in, for example, WO9850399, WO0134617, WO0212258, WO3065806, WO04062599, WO06016997, WO0612425, WO03066065, and WO0190129. Such molecules have also been described in the scientific and patent literature as lipid A mimetics. Lipid A mimetics suitably share some functional and/or structural activity with lipid A, and in one aspect are recognised by TLR4 receptors. AGPs as described herein are sometimes referred to as lipid A mimetics in the art. In a preferred embodiment, the TLR4 agonist is 3D-MPL. TLR4 agonists, such as 3-O-deacylated monophosphoryl lipid A (3D-MPL), and their use as adjuvants in vaccines has e.g. been described in WO 96/33739 and WO2007/068907 and reviewed in Alving et al. (2012) Curr Opin in Immunol 24:310.

In a further embodiment of the method of the invention, the first adjuvant and the second adjuvant comprise an immunologically active saponin, such as an immunologically active saponin fraction, such as QS21.

Adjuvants comprising saponins have been described in the art. Saponins are described in: Lacaille-Dubois and Wagner (1996) A review of the biological and pharmacological activities of saponins. Phytomedicine vol 2:363. Saponins are known as adjuvants in vaccines. For example, Quil A (derived from the bark of the South American tree Quillaja Saponaria Molina), was described by Dalsgaard et al. in 1974 ("Saponin adjuvants", Archiv. fur die gesamte Virusforschung, Vol. 44, Springer Verlag, Berlin, 243) to have adjuvant activity. Purified fractions of Quil A have been isolated by HPLC which retain adjuvant activity without the toxicity associated with Quil A (Kensil et al. (1991) J. Immunol. 146: 431. Quil A fractions are also described in U.S. Pat. No. 5,057,540 and "Saponins as vaccine adjuvants", Kensil, C. R., Crit Rev Ther Drug Carrier Syst, 1996, 12 (1-2):1-55.

Two such fractions, suitable for use in the present invention, are QS7 and QS21 (also known as QA-7 and QA-21). QS21 is a preferred immunologically active saponin fraction for use in the present invention. QS21 has been reviewed in Kensil (2000) In O'Hagan: Vaccine Adjuvants: preparation methods and research protocols. Homana Press, Totowa, N.J., Chapter 15. Particulate adjuvant systems comprising fractions of Quil A, such as QS21 and QS7, are e.g. described in WO 96/33739, WO 96/11711 and WO2007/068907.

In addition to the other components, the adjuvant preferably comprises a sterol. The presence of a sterol may further reduce reactogenicity of compositions comprising saponins, see e.g. EP0822831. Suitable sterols include beta-sitosterol, stigmasterol, ergosterol, ergocalciferol and cholesterol. Cholesterol is particularly suitable. Suitably, the immunologically active saponin fraction is QS21 and the ratio of QS21:sterol is from 1:100 to 1:1 w/w, such as from 1:10 to 1:1 w/w, e.g. from 1:5 to 1:1 w/w.

In a preferred embodiment of the method of the invention, the TLR4 agonist is 3D-MPL and the immunologically active saponin is QS21.

In some embodiments, the adjuvant is presented in the form of an oil-in-water emulsion, e.g. comprising squalene, alpha-tocopherol and a surfactant (see e.g. WO95/17210) or in the form of a liposome. A liposomal presentation is preferred.

The term "liposome" when used herein refers to uni- or multilamellar (particularly 2, 3, 4, 5, 6, 7, 8, 9, or 10 lamellar depending on the number of lipid membranes formed) lipid structures enclosing an aqueous interior. Liposomes and liposome formulations are well known in the art. Liposomel presentations are e.g. described in WO 96/33739 and WO2007/068907. Lipids which are capable of forming liposomes include all substances having fatty or fat-like properties. Lipids which can make up the lipids in the liposomes may be selected from the group comprising glycerides, glycerophospholipides, glycerophosphinolipids, glycerophosphonolipids, sulfolipids, sphingolipids, phospholipids, isoprenolides, steroids, stearines, sterols, archeolipids, synthetic cationic lipids and carbohydrate containing lipids. In a particular embodiment of the invention the liposomes comprise a phospholipid. Suitable phospholipids include (but are not limited to): phosphocholine (PC) which is an intermediate in the synthesis of phosphatidylcholine; natural phospholipid derivates: egg phosphocholine, egg phosphocholine, soy phosphocholine, hydrogenated soy phosphocholine, sphingomyelin as natural phospholipids; and synthetic phospholipid derivates: phosphocholine (didecanoyl-L-a-phosphatidylcholine [DDPC], dilauroylphosphatidylcholine [DLPC], dimyristoylphosphatidylcholine [DMPC], dipalmitoyl phosphatidylcholine [DPPC], Distearoyl phosphatidylcholine [DSPC], Dioleoyl phosphatidylcholine, [DOPC], 1-palmitoyl, 2-oleoylphosphatidylcholine [POPC], Dielaidoyl phosphatidylcholine [DEPC]), phosphoglycerol (1,2-Dimyristoyl-sn-glycero-3-phosphoglycerol [DMPG], 1,2-dipalmitoyl-sn-glycero-3-phosphoglycerol [DPPG], 1,2-distearoyl-sn-glycero-3-phosphoglycerol [DSPG], 1-palmitoyl-2-oleoyl-sn-glycero-3-phosphoglycerol [POPG]), phosphatidic acid (1,2-dimyristoyl-sn-glycero-3-phosphatidic acid [DMPA], dipalmitoyl phosphatidic acid [DPPA], distearoyl-phosphatidic acid [DSPA]), phosphoethanolamine (1,2-dimyristoyl-sn-glycero-3-phosphoethanolamine [DMPE], 1,2-Dipalmitoyl-sn-glycero-3-phosphoethanolamine [DPPE], 1,2-distearoyl-sn-glycero-3-phosphoethanolamine [DSPE], 1,2-Dioleoyl-sn-Glycero-3-Phosphoethanolamine [DOPE]), phoshoserine, polyethylene glycol [PEG] phospholipid.

Liposome size may vary from 30 nm to several um depending on the phospholipid composition and the method used for their preparation. In particular embodiments of the invention, the liposome size will be in the range of 50 nm to 500 nm and in further embodiments 50 nm to 200 nm. Dynamic laser light scattering is a method used to measure the size of liposomes well known to those skilled in the art.

In a particularly suitable embodiment, liposomes used in the invention comprise DOPC and a sterol, in particular cholesterol. Thus, in a particular embodiment, compositions of the invention comprise QS21 in any amount described herein in the form of a liposome, wherein said liposome comprises DOPC and a sterol, in particular cholesterol.

Preferably, the first adjuvant and second adjuvant comprise 3D-MPL and QS21 in a liposomal formulation.

In one embodiment, the first adjuvant comprises between 12.5 and 75 micrograms of 3D-MPL and between 12.5 and 75 micrograms of QS21 in a liposomal formulation, and the second adjuvant comprises between 12.5 and 75 micrograms of 3D-MPL and between 12.5 and 75, micrograms of QS21 in a liposomal formulation.

In another embodiment, the first adjuvant comprises between 12.5 and 37.5, such as between 20 and 30 micrograms (for example about or exactly 25 micrograms), of 3D-MPL and between 12.5 and 37.5, such as between 20 and 30 micrograms (for example about or exactly 25 micrograms) of QS21 in a liposomal formulation and the second adjuvant comprises between 12.5 and 37.5, such as between 20 and 30 micrograms (for example about or exactly 25 micrograms), of 3D-MPL and between 12.5 and 37.5, such as between 20 and 30 micrograms (for example about or exactly 25 micrograms), of QS21 in a liposomal formulation. Suitably in first and second adjuvants the amount of 3D-MPL is the same as the amount of QS21.

In another embodiment, the first adjuvant comprises between 12.5 and 37.5, such as between 20 and 30 micrograms (for example about or exactly 25 micrograms) 3D-MPL and between 12.5 and 37.5, such as between 20 and 30 micrograms (for example about or exactly 25 micrograms) QS21 in a liposomal formulation and the second adjuvant comprises between 2.5 and 7.5, such as 5 micrograms, of 3D-MPL and between 2.5 and 7.5, such as 5 micrograms of QS21 in a liposomal formulation.

In another embodiment, the first adjuvant comprises between 12.5 and 37.5, such as between 20 and 30 micrograms (for example about or exactly 25 micrograms) of 3D-MPL and between 12.5 and 37.5, such as between 20 and 30 micrograms (for example about or exactly 25 micrograms) of QS21 in a liposomal formulation and the second adjuvant comprises a reduced amount of 3D-MPL or QS21, such as between 2.5 and 20, such as between 2.5 and 10 micrograms (for example about or exactly 5 micrograms) of 3D-MPL and such as between 2.5 and 20, such as between 2.5 and 10 micrograms (for example about or exactly 5 micrograms) of QS21 in a liposomal formulation. Suitably in first and second adjuvants the amount of 3D-MPL is the same as the amount of QS21.

It is well known that for parenteral administration solutions should be physiologically isotonic (i.e. have a pharmaceutically acceptable osmolality) to avoid cell distortion or lysis. A pharmaceutically acceptable osmolality will generally mean that solutions will have an osmolality which is approximately isotonic or mildly hypertonic. Suitably the immunogenic compositions of the present invention will have an osmolality in the range of 250 to 750 mOsm/kg, for example, the osmolality may be in the range of 250 to 550 mOsm/kg, such as in the range of 280 to 500 mOsm/kg. Osmolality may be measured according to techniques known in the art, such as by the use of a commercially available osmometer, for example the Advanced® Model 2020 available from Advanced Instruments Inc. (USA). An "isotonicity agent" is a compound that is physiologically tolerated and imparts a suitable tonicity to a formulation (e.g. immunogenic compositions of the invention) to prevent the net flow of water across cell membranes that are in contact with the formulation. Aqueous adjuvant compositions are known which contain 100 mM sodium chloride or more, for example adjuvant system A (ASA) in WO 2005/112991 and WO2008/142133 or the liposomal adjuvants disclosed in WO2007/068907.

In some embodiments, the isotonicity agent used for the composition is a salt. In other embodiments, however, the composition comprises a non-ionic isotonicity agent and the concentration of sodium chloride or the ionic strength in the composition is less than 100 mM, such as less than 80 mM, e.g. less than 30 mM, such as less 10 mM or less than 5 mM. In a preferred embodiment, the non-ionic isotonicity agent is a polyol, such as sorbitol. The concentration of sorbitol may e.g. between about 3% and about 15% (w/v), such as between about 4% and about 10% (w/v). Adjuvants comprising an immunologically active saponin fraction and a TLR4 agonist wherein the isotonicity agent is salt or a polyol have been described in WO2012/080369 which is incorporated herein by reference.

In a further embodiment, first adjuvant and/or the second adjuvant does not comprise aluminium.

The pH of the immunogenic compositions should be suitable for parenteral administration. Typically the pH will be in the range 7.0 to 9.0, especially 7.25 to 8.75, such as 7.5 to 8.5, in particular pH 7.75 to 8.25. A pH of about 8.0 is of particular interest.

Immunisation Regimes, Target Populations and Modes of Administration

In one embodiment the subject receives two doses of immunogenic compositions comprising an M72 antigen within a two year period or alternatively within a five year period. In a second embodiment the subject receives three doses of immunogenic compositions comprising an M72 antigen within a two year period or alternatively within a five year period.

When the subject receives two doses of immunogenic compositions comprising an M72 antigen within a five year period, this will be the first immunogenic composition and the second immunogenic composition. In one embodiment, the time interval between administration of the first composition and administration of the second composition is between 2 months and 5 years, such as between 3 months and 5 years, such as between 3 months and 24 months, e.g. between 3 and 18 months, such as between 3 and 14 months. In some embodiments the time interval between the administration of the first composition and administration of the second composition is between 3 and 10 months, e.g. between 3 and 9 months, such as between 3 and 8 months. In some embodiments the time interval between the administration of the first composition and administration of the second composition is between 4 and 14 months, e.g. between 4 and 9 months, such as between 4 and 8 months.

When the subject receives three doses of immunogenic compositions comprising an M72 antigen within a five year period, this may be (a) two doses of the first immunogenic composition and one dose of the second immunogenic composition or it may be (b) may be one dose of the first immunogenic composition and two doses of the second immunogenic composition.

In one embodiment of (a), the time interval between initial administration of the first composition and administration of the second composition is between 3 months and 5 years, such as between 3 months and 24 months, e.g. between 3 and 18 months, such as between 3 and 14 months. In some embodiments the time interval between the initial administration of the first composition and administration of the second composition is between 3 and 10 months, e.g. between 3 and 9 months, such as between 3 and 8 months. In some embodiments the time interval between the initial administration of the first composition and administration of the second composition is between 4 and 14 months, e.g. between 4 and 9 months, such as between 4 and 8 months. In another embodiment of (a), the time interval between final administration of the first composition and administration of the second composition is between 2 months and 5 years, such as between 3 months and 5 years, such as between 3 months and 24 months, e.g. between 3 and 18 months, such as between 3 and 14 months. In some embodiments the time interval between the final administration of the first composition and administration of the second composition is between 3 and 10 months, e.g. between 3 and 9 months, such as between 3 and 8 months. In some embodiments the time interval between the final administration of the first composition and administration of the second composition is between 4 and 14 months, e.g. between 4 and 9 months, such as between 4 and 8 months.

In one embodiment of (b), the time interval between administration of the first composition and final administration of the second composition is between 3 months and 5 years, such as between 3 months and 24 months, e.g. between 3 and 18 months, such as between 3 and 14 months. In some embodiments the time interval between the administration of the first composition and final administration of the second composition is between 3 and 10 months, e.g. between 3 and 9 months, such as between 3 and 8 months. In some embodiments the time interval between the administration of the first composition and final administration of the second composition is between 4 and 14 months, e.g. between 4 and 9 months, such as between 4 and 8 months. In another embodiment of (b), the time interval between administration of the first composition and initial administration of the second composition is between 2 months and 5 years, such as between 3 months and 5 years, such as between 3 months and 24 months, e.g. between 3 and 18 months, such as between 3 and 14 months. In some embodiments the time interval between the administration of the first composition and final administration of the second composition is between 3 and 10 months, e.g. between 3 and 9 months, such as between 3 and 8 months. In some embodiments the time interval between the administration of the first composition and final administration of the second composition is between 4 and 14 months, e.g. between 4 and 9 months, such as between 4 and 8 months.

Where the subject is administered the first composition twice, the time interval between initial administration of the first composition and further administration of the first composition may be between 2 weeks and 2 months.

Where the subject is administered the second composition twice, the time interval between initial administration of the second composition and further administration of the second composition may be between 3 months and 5 years, such as between 3 months and 24 months, such as between 6 and 14 months.

In a further embodiment, the second composition could e.g. be given as a recurrent yearly booster, e.g. for 1-5 years or more. In one embodiment, at a time interval of at least 12, at least 13, at least 14, at least 15, at least 16, at least 17, at least 18, at least 19, or at least 20, or more months after administration of the second composition, the second composition is administered one or more further times.

The subject to be treated using the method of the invention may be of any age. In one aspect of the invention, the subject is human.

In one embodiment the subject is an adult human (typically aged 18-60).

The first and second compositions may be administered via various suitable routes, including parenteral, such as intramuscular or subcutaneous administration.

In one particular embodiment, the second composition is administered intradermally. The term intradermally as used herein is intended to refer to the application of antigens into the dermis and/or epidermis of human skin. Intradermal application of an immunogenic composition may be performed by using any cutaneous method known to the skilled person including, but not limited to, delivery using a short needle device (a device comprising a microneedle that is between about 0.2 and about 0.6 mm in length) or delivery using a skin patch. Suitable devices for use with the cutaneous vaccines described herein include short needle devices such as those described in U.S. Pat. Nos. 4,886,499, 5,190,521, 5,328,483, 5,527,288, 4,270,537, 5,015,235, 5,141,496, 5,417,662 and EP1092444. Cutaneous vaccines may also be administered by devices which limit the effective penetration length of a needle into the skin, such as those described in WO99/34850. Also suitable are jet injection devices which deliver liquid vaccines to the dermis via a liquid jet injector or via a needle. Also suitable are ballistic powder/particle delivery devices which use compressed gas to accelerate vaccine in powder form through the outer layers of the skin to the dermis. Skin patches will generally comprise a backing plate which includes a solid substrate. Patches deliver the antigen and adjuvant used in the invention to the dermis or epidermis. In particular embodiment, the patches useful in the present invention comprise a plurality of microprojections. The microprojections may be of any shape suitable for piercing the stratum corneum, epidermis and/or dermis and delivery and antigen and adjuvant to the epidermis or dermis. In a particular embodiment, microprojections are biodegradable and comprise a biodegradable polymer.

Immunogenic compositions used in the invention may be made by admixing the antigen(s) and the adjuvant. The antigen(s) may be provided in a lyophilized form or in a liquid formulation. For each composition, a kit may be provided comprising a first container comprising the antigen and a second container comprising the adjuvant.

Suitably, the immunogenic compositions according to the present invention have a human dose volume of between 0.05 ml and 1 ml, such as between 0.1 and 0.5 ml, in particular a dose volume of about 0.5 ml, or 0.7 ml. The volume of the second immunogenic composition may be reduced, and e.g. be between 0.05 ml and 0.5 ml, such as between 0.1 and 0.2 ml. The volumes of the compositions used may depend on the delivery route with smaller doses being given by the intradermal route.

The teaching of all references in the present application, including patent applications and granted patents, are herein fully incorporated by reference. A composition or method or process defined as "comprising" certain elements is understood to encompass a composition, method or process (respectively) consisting of those elements. The invention will be further described by reference to the following, non-limiting, example:

Example 1: Vaccination Using M72 and Adjuvant AS01

The impact of delayed and reduced dosages of the tuberculosis antigen M72 2-his (SEQ ID No. 2) was investigated in a mouse model.

Material and Methods

Animal Model

Female mouse C57BL/6JOlaHsd—6 weeks old—12 mice per group—were injected by the intramuscular route with 50 μl at days 0-14 and 28 or 98 as indicated in table below.

| Group | Dose 1 D0 | Dose 2 D14 | Dose 3 D28 | Dose 3 D98 |
|---|---|---|---|---|
| G1 | 0.25 ug M72 AS01E | 0.25 ug M72 AS01E | 0.25 ug M72 AS01E | |
| G2 | | | 0.05 ug M72 1/5th AS01E | |
| G3 | | | 0.01 ug M72 1/25th AS01E | |
| G4 | | | | 0.25 ug M72 AS01E |
| G5 | | | | 0.05 ug M72 1/5th AS01E |
| G6 | | | | 0.01 ug M72 1/25th AS01E |
| G7 | | | | 0.25 ug M72 alone |

AS01E adjuvant contained the immunostimulants 3D-MPL® (GlaxoSmithKline Biologicals, Montana, USA) and QS21 (2.5 ug of each) in a formulation with liposomes. Dilutions were performed using the adjuvant buffer.

Read-out:

Whole Blood ICS at
    day 21-7 days Post-II (G1-7);
    day 35-7 days Post-III (G1-3);
    day 105-77 days Post-III (G1-3) and 7 days Post-III (G4-7)

Serology anti-M72 IgTot at
    day 28-14 days Post-II (G1-7)
    day 42-14 days Post-III (G1-3)
    day 112-84 days Post III (G1-3) and 14 days Post III (G4-7)

In order to have sufficient volume, the whole blood of 4 pools of 3 mice for groups was collected at days 21, 35 and 105. Individual sera were collected at days 28, 42 and 112. The mice were individually identified in order to link PII and PIII results for ICS and serology.

Read-Out(s) Description

Cellular Immune Response-Intracellular Cytokine Staining (ICS)

Leukocyte Isolation

At each time point, blood was collected from each mouse and subsequently pooled (5 pools of 3 mice). Blood was collected in tubes containing, RPMI/additives (RPMI 1640, supplemented with Glutamine, Penicillin/streptomycin, Sodium Pyruvate, non-essential amino-acids and 2-mercaptoethanol) containing heparin (1/10). Ten volumes of Lysing buffer were added to the whole blood and tubes were incubated at room temperature (RT) for 10 min. After centrifugation (335 g, 10 min at RT), the pellet was harvested in RPMI/additives and filtered (Cell strainer 100 µm). Cells were pelleted again (335 g, 10 min at RT) and resuspended in Complete Medium (RPMI 1640, supplemented with Glutamine, Penicillin/streptomycin, Sodium Pyruvate, non-essential amino-acids and 2-mercaptoethanol, and 5% Heat inactivated Fetal Calf Serum).

In Vitro Stimulation of Fresh Leukocytes

Leukocytes were plated in round bottom 96-well plates at approximately 1 million cells per well. Leukocytes were then stimulated for 6 hours (37° C., 5% CO2) with anti-CD28 (clone 9C10 (MFR4.B) and anti-CD49d (clone 37.51) at 1 µg/ml, with or without 1 µg/ml of peptides covering the M72 sequence. After a 2 hour-stimulation, Brefeldin A diluted 1/200 in complete medium was added for 4 additional hours. Plates were then transferred at 4° C., overnight.

ICS

Cells were stained and analyzed using a 5-colour ICS assay.

Cells were transferred to V-bottom 96-well plates, centrifuged at 189 g for 5 min at 4° C. after wash with 200 µl Flow Buffer (PBS 1×, 1% FCS), resuspended the cells in 50 µl Flow Buffer containing anti-CD16/32 (clone 2.4G2) diluted 1/50, for 10 min at 4° C. Then, 50 µl Flow Buffer containing anti-CD4-V450 (clone RM4-5, diluted 1/50) and anti-CD8-PerCp-Cy5.5 (clone 53-6.7, diluted 1/50) antibodies and Live&Death PO (diluted 1/500) was added for 30 min at 4° C. Cells were centrifuged (189 g for 5 min at 4° C.) and washed with 200 µl Flow Buffer.

Leukocytes were fixed and permeabilized by adding 200 µl of Cytofix/Cytoperm solution (Becton Dickinson commercial buffer) for 20 min at 4° C. Cells were centrifuged (189 g for 5 min at 4° C.) and washed with 200 µl Perm/Wash buffer (Becton Dickinson commercial buffer diluted 1:10 in distilled water). After an additional centrifugation step, cells were stained in 50 µl Perm/Wash buffer with anti-IL2-FITC (clone JES6-5H4, diluted 1/400), anti-IFNγ-APC (clone XMG1.2, diluted 1/50) and anti-TNFα-PE (clone MP6-XT22, diluted 1/700) antibodies, for 1 hour at 4° C. Cells were washed twice with the Perm/Wash buffer resuspended in 220 µl BD Stabilizing Fixative solution. Stained cells were analyzed by flow cytometry using a LSRII and the FlowJo software.

Humoral Response-Anti-M72 Ig Tot Serology by Elisa 96-well Elisa plates were coated with the recombinant antigen M72 at 0.25 µg/ml in PBS and incubated overnight at 4° C. Sera from vaccinated mice at Post II and Post III were diluted at 1/10000, in PBS (0.2%)-BSA and then a 2 fold serial dilution is performed from well 1 to 12 and incubated. Serial dilutions of the standard and control material were used to calculate the anti-M72 antibody standard titers of tested sera and to ensure validity of the test. Plates were washed with PBS 0.1% tween20 buffer after each incubation step. A biotinylated goat antibody specific for mice Ig is then added and the antigen-antibody complex is revealed by incubation with a streptavidin-peroxidase complex and a peroxidase substrate ortho-phenylenediamine dihydrochlorid/H2O2. The Optical densities (O.D.) were recorded at 490-620 nm. The anti-M72 antibody titer of each individual mouse serum is determined from the standard curve of the ELISA using a regression model and expressed in ELISA unit (EU)/ml. Geometric Mean Titers (GMT) are then calculated for each group of mice.

Results

T Cell Responses

A. Kinetics of the M72-Specific CD4 T & CD8 T Cells Responses

To evaluate a potential benefit of the fractional and/or or delayed third dose on the CD4 T and CD8 T cell response, mice were immunized with a maximal dose of 0.25 ug M72 in the current study in order to be in the dynamic range of the CD4 T cell response while inducing a detectable CD8 T cell response.

As shown in FIG. 1, giving a fractional third dose in the standard schedule (D0-D14-D28) did not provide an improved CD4 T cell response as comparable boosts were observed from 7PII to 7PIII in groups receiving a full dose, $1/5^{th}$ and $1/25^{th}$ of the dose.

However, despite some variability of the M72 specific CD4 T cell response between pools, a greater boost was observed 7 days after a delayed third dose of 0.25 ug of M72 as compared to the standard schedule. Furthermore, the level of M72 specific CD4 T cell response in mice receiving a delayed and fractional third dose or a delayed and unadjuvanted third dose was comparable to the levels observed in group immunized with the full dose in the standard schedule. This suggests a benefit of a delayed schedule in terms of the level of the CD4 T cell response.

Figure 2:
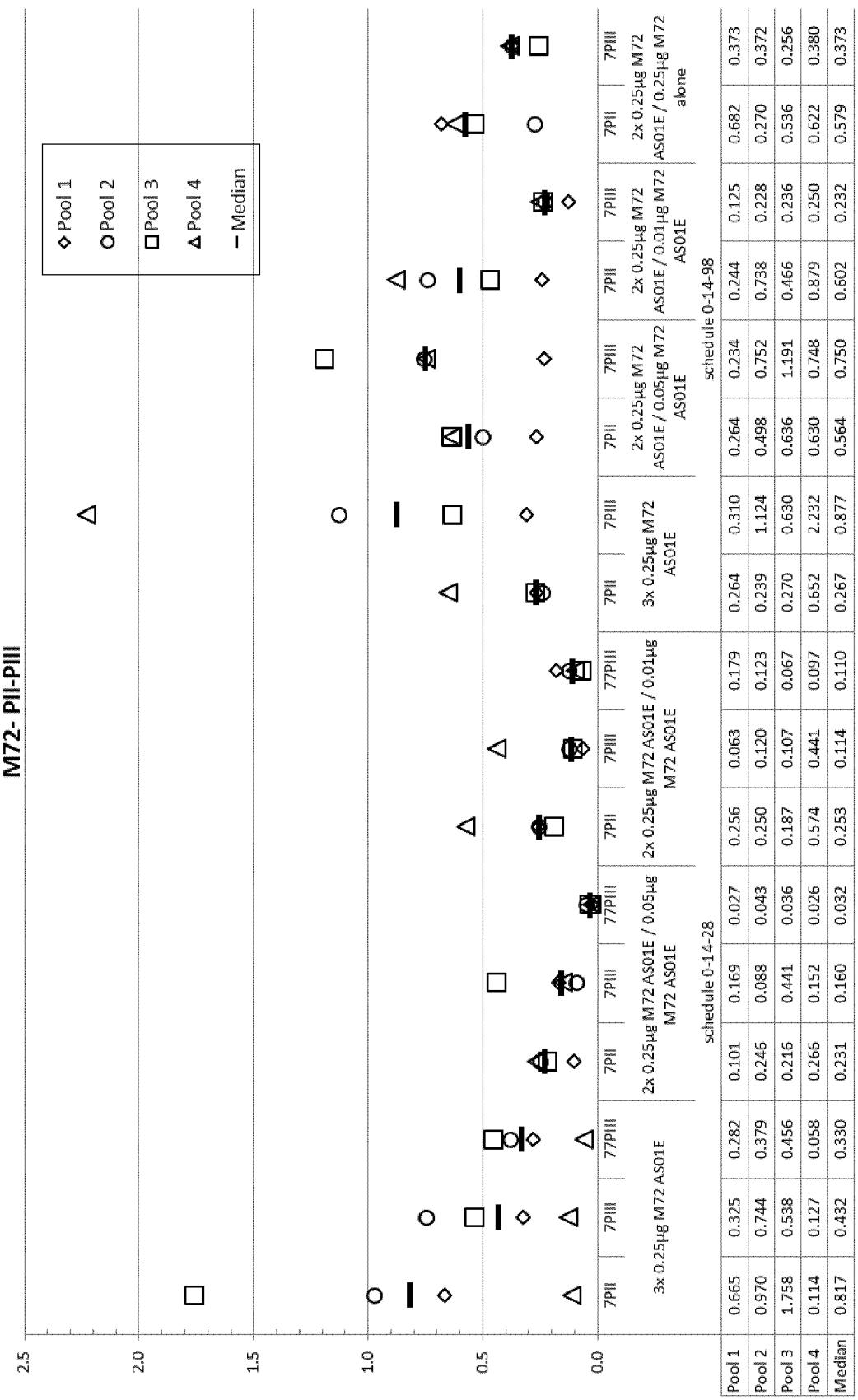
FIG. 2: CD8 T cell responses from mice administered M72 in standard and delayed regimes

Low levels of M72-specific CD8 T cells response were detected in mice that received 0.25 ug M72 dose in the standard schedule and the third immunization dose failed to boost the M72-specific CD8 T cell response (FIG. 2)

A decreased M72-specific CD8 T cell response was observed in mice that received a fractional third dose in the standard schedule. This is in line with previous data (not shown) where the CD8 T cell response was largely affected by the dose range of M72 protein used for immunizing the mice and where higher dose of M72 (1 ug or 8 ug) induced a higher level of response than 0.1 ug or 0.25 ug of M72.

In mice that received a delayed third dose of 0.25 ug of M72, a boost of the M72 specific CD8 T cell response was seen from 7PII to 7PIII in all tested pools. However, medians of the CD8 T cell response showed variability between groups at 7PII (from 0.231 to 0.817) despite the fact that all groups received 2 doses of 0.25 ug of M72/ASO1E.

B. Cytokine Profile of the M72-Specific CD4 & CD8 T Cells Responses

Similar CD4 T cytokine expression profiles was observed in groups receiving a full dose, $1/5^{th}$ and $1/25^{th}$ of the dose in the standard schedule at both 7PII and 7PIII. The M72-specific CD4 T cell response included triple (IL2/IFNg/TNFa) and double (IFNg/TNFa) after 2 immunizations. The third immunization dose failed to support the progression of polyfunctional CD4 Th1 cells and instead increased the double (1L2/IFNg) and single (IFNg only) producing CD4 T cells (FIG. 3).

Figure 3:
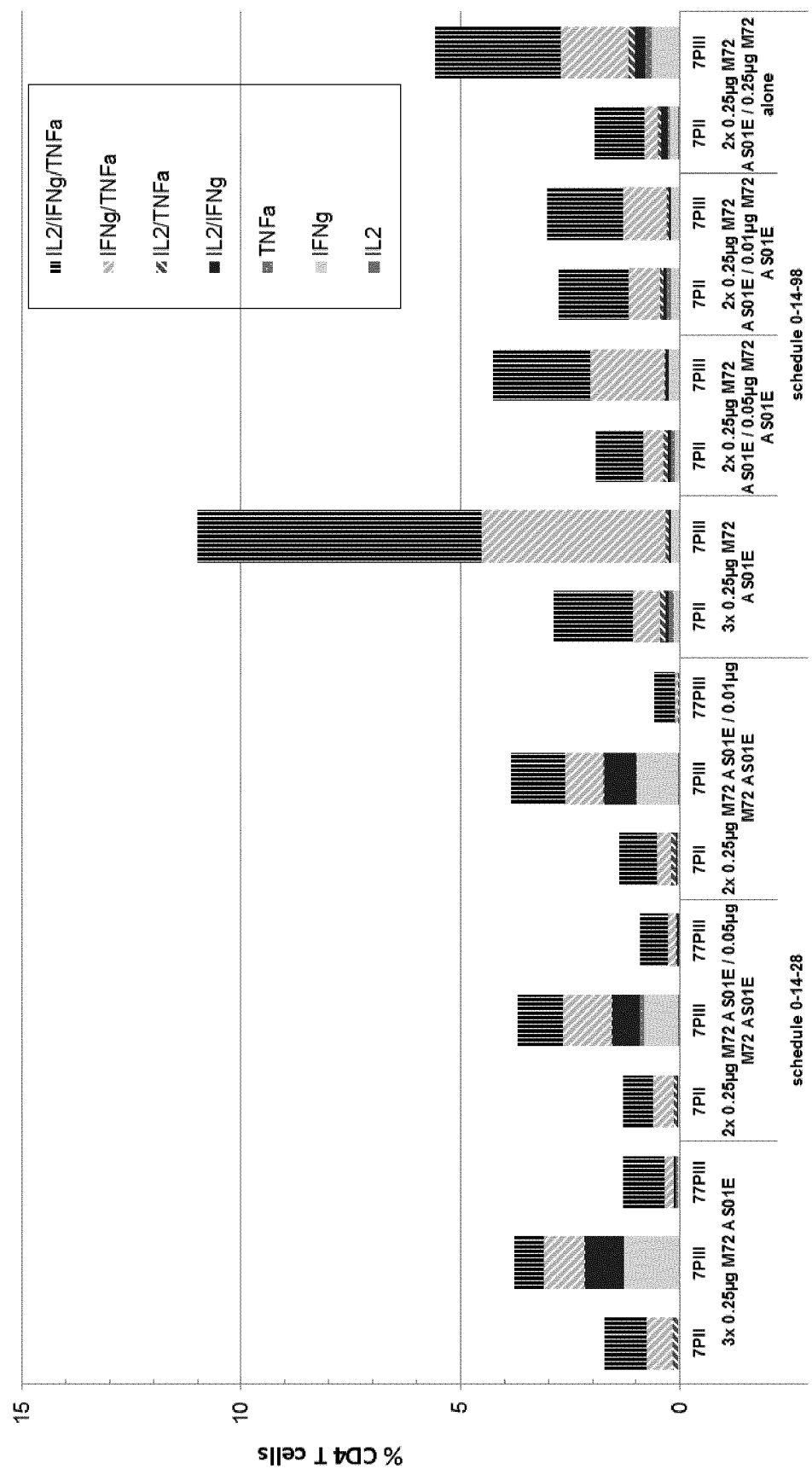
FIG. 3: CD4 T cell cytokine profile from mice administered M72 in standard and delayed regimes

Giving a delayed third dose seems to support the progression of polyfunctional CD4 Th2 cells as the M72-specific CD4 T cell response is mostly composed of IL2/IFNg/TNFa and IFNg/TNFa producing CD4 T cells (FIG. 3). AS01 further enhanced the progression of polyfunctional T cells as reduced level of IL2/IFNg/TNFa and IFNg/TNFa and increased levels of IFNg only producing CD4 T cells were observed in mice that received a delayed and unadjuvanted third dose.

Even though the level of M72 specific CD4 T cell response in mice receiving a delayed and fractional third dose is similar to what is observed with the benchmark, the cytokine profile is slightly different and altogether these data suggests an improved progression of the polyfunctional CD4 Th1 cells in a delayed immunization schedule.

The magnitude and quality of multifunctional CD4 T cells has been shown to be a correlate of protection in mice (Derrick et al 2011 *Vaccine* 29:2902-2909).

Figure 4:
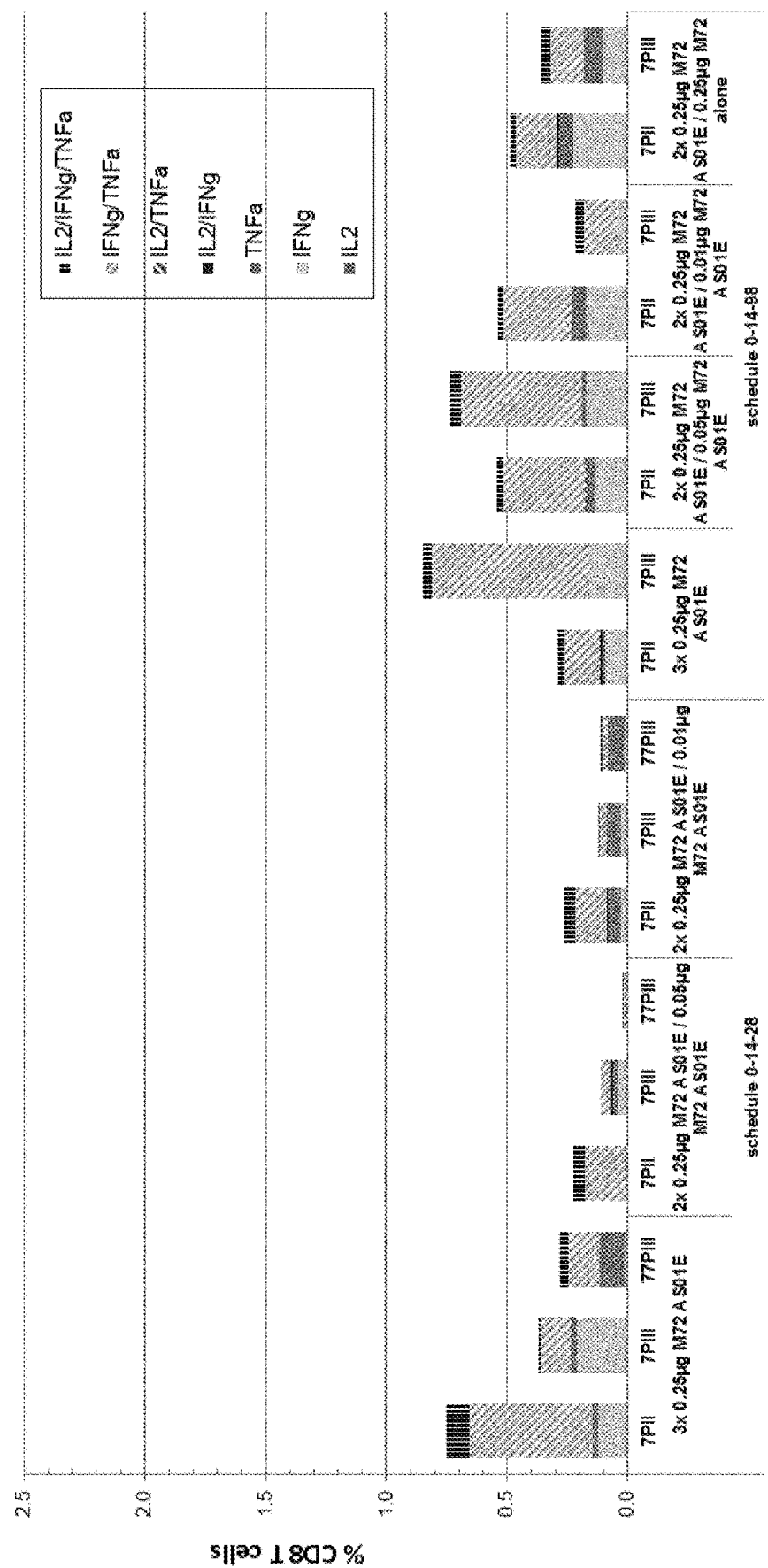
FIG. 4: CD8 T cell cytokine profile from mice administered M72 in standard and delayed regimes

Similar M72-specific CD8 T cell cytokine profiles were observed across all groups at both 7PII and 7PIII (FIG. 4). The M72-specific CD8 T cell responses were mostly composed of double (IFNg/TNFa) and single (IFNg only) producing CD8 T cells. Very low levels of IL2/INFg/TNFa and TNFa producing CD8 T cell were also detected.

Antibody Responses

A. Anti-M72 Ig Tot Serology

Figure 5:
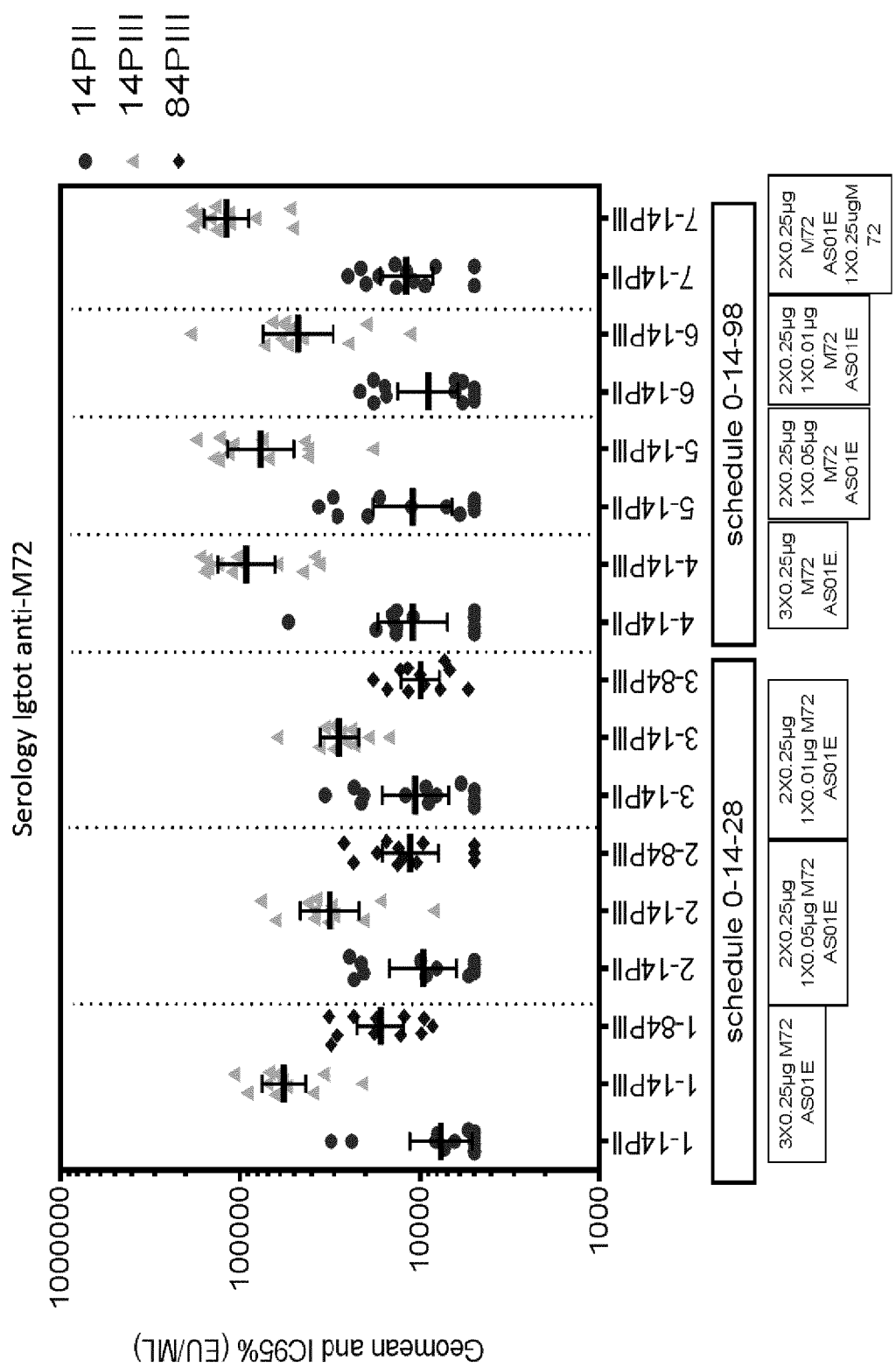
FIG. 5: Anti M72 serology from mice administered M72 in standard and delayed regimes

As shown in FIG. 5, a boost of the anti M72 serology response was observed between 14PII and 14 PIII in groups receiving a full dose, $\frac{1}{5}^{th}$ and $\frac{1}{25}^{th}$ of the dose in the standard schedule. A trend of a dose-range effect was observed with the highest dose giving the highest M72 specific serology response. The persistence of the response decreased over time as shown by the lower serology response at 84PIII.

In mice that received a delayed third immunization, a higher magnitude of the response was observed. Similar levels of M72 specific Ig were seen in the presence and absence of AS01E, suggesting that the M72 alone is sufficient to induce a high serology response after a delayed third immunization.

The invention claimed is:

1. A method for inducing an immune response in a subject comprising:

(i) administration of a dose of a first immunogenic composition comprising a polypeptide sequence having at least 90% identity to SEQ ID NO:1 and a first adjuvant, wherein the first adjuvant comprises a TLR agonist, an immunologically active saponin, or both to the subject; followed by (ii) administration of a dose of a second immunogenic composition comprising a polypeptide sequence having at least 90% identity to SEQ ID NO:1 to the subject;

and wherein the subject receives a total of three doses of immunogenic compositions within a five year period; wherein the subject receives two doses of the first immunogenic composition and one dose of the second immunogenic composition, where the time interval between the final administration of the first composition and administration of the second composition is between 3 months and 5 years.

2. The method of claim 1, wherein the subject receives either (i) an additional dose of the first immunogenic composition or (ii) an additional dose of the second immunogenic composition, and wherein the subject receives a total of three doses within 2 years.

3. The method of claim 1, wherein the time interval between the initial administration of the dose of the first composition and administration of the dose of the second composition is between 4 and 14 months.

4. The method of claim 1, wherein the time interval between the final administration of the dose of the first composition and administration of the dose of the second composition is between 4 and 14 months.

5. The method of claim 1, wherein the dose of the first immunogenic composition comprises between 1 ug and 100 ug of polypeptide sequence having at least 90% identity to SEQ ID NO:1 and the dose of the second immunogenic composition comprises between 1 ug and 100 ug of polypeptide sequence having at least 90% identity to SEQ ID NO:1.

6. The method of claim 5, wherein the dose of the second immunogenic composition comprises between 5 ug and 50 ug of polypeptide sequence having at least 90% identity to SEQ ID NO:1.

7. The method of claim 5, wherein the dose of the second immunogenic composition comprises between 1 ug and 8 ug of polypeptide sequence having at least 90% identity to SEQ ID NO:1.

8. The method of claim 5, wherein the dose of the first immunogenic composition and the dose of the second immunogenic composition together comprise between 1 ug and 100 ug of protein antigen in total.

9. The method of claim 1, wherein the subject is in need of the amelioration of infection by mycobacteria.

10. The method of claim 1, wherein the subject is human.

11. The method of claim 1, wherein the subject is in need of the amelioration of infection by *Mycobacterium tuberculosis*.

12. The method of claim 1, wherein the subject is in need of the prophylaxis, treatment or amelioration of infection by mycobacteria.

* * * * *